US 11,786,378 B2

(12) United States Patent
Slater

(10) Patent No.: US 11,786,378 B2
(45) Date of Patent: Oct. 17, 2023

(54) ACETABULAR CUP EXTRACTOR

(71) Applicant: Shukla Medical, St. Petersburg, FL (US)

(72) Inventor: Stephen Slater, Morris Plains, NJ (US)

(73) Assignee: Shukla Medical, St. Petersburg, FL (US)

(*) Notice: Subject to any disclaimer, the term of this patent is extended or adjusted under 35 U.S.C. 154(b) by 159 days.

(21) Appl. No.: 17/165,535

(22) Filed: Feb. 2, 2021

(65) Prior Publication Data

US 2021/0154025 A1 May 27, 2021

Related U.S. Application Data

(63) Continuation of application No. 16/087,144, filed as application No. PCT/US2017/026975 on Apr. 11, 2017, now Pat. No. 10,905,564.

(60) Provisional application No. 62/321,425, filed on Apr. 12, 2016.

(51) Int. Cl.
A61F 2/46 (2006.01)
(52) U.S. Cl.
CPC .... *A61F 2/4609* (2013.01); *A61F 2002/4619* (2013.01); *A61F 2002/4622* (2013.01)
(58) Field of Classification Search
CPC ........ A61F 2/46; A61F 2/4605; A61F 2/4609; A61F 2002/4619; A61F 2002/4622; A61F 2002/4625; A61F 2002/4681
See application file for complete search history.

(56) References Cited

U.S. PATENT DOCUMENTS

| | | | | |
|---|---|---|---|---|
| 5,830,215 A * | 11/1998 | Incavo | ............... | A61B 17/92 606/99 |
| 6,063,123 A * | 5/2000 | Burrows | ............... | A61F 2/34 606/86 R |
| 6,063,124 A * | 5/2000 | Amstutz | ............... | A61F 2/3603 623/22.21 |
| 6,565,575 B2 * | 5/2003 | Lewis | ............... | A61F 2/4609 606/99 |
| 6,565,757 B1 | 5/2003 | Wedkamp | | |
| 7,744,602 B2 * | 6/2010 | Teeny | ............... | A61F 2/4609 606/100 |
| 7,763,031 B2 | 7/2010 | Tulkis | | |
| 7,927,376 B2 * | 4/2011 | Leisinger | ............... | A61F 2/4637 606/91 |
| 8,834,480 B2 * | 9/2014 | Hudak, Jr. | ............... | A61F 2/4609 606/86 R |

(Continued)

FOREIGN PATENT DOCUMENTS

| | | |
|---|---|---|
| WO | 2014063197 A1 | 5/2014 |
| WO | 2015155657 A1 | 10/2015 |

(Continued)

OTHER PUBLICATIONS

Written Opinion of the International Searching Authority regarding PCT/US2017/026975, dated Jul. 18, 2017.

(Continued)

*Primary Examiner* — Eric S Gibson
(74) *Attorney, Agent, or Firm* — Kim IP Law Group LLC

(57) ABSTRACT

An acetabular cup extractor is provided that is designed for extracting medical device implants. The acetabular cup extractor includes a fastener for securing to an implant and a cutting assembly. The cutting assembly further includes a blade spaced and movably connected to the fastener and a handle operatively connected to the blade.

6 Claims, 12 Drawing Sheets

(56) References Cited

U.S. PATENT DOCUMENTS

| | | | |
|---|---|---|---|
| 10,653,534 B2* | 5/2020 | Joo | A61F 2/34 |
| 10,905,564 B2* | 2/2021 | Slater | A61F 2/4609 |
| 2002/0116007 A1* | 8/2002 | Lewis | A61F 2/4609 |
| | | | 606/99 |
| 2006/0195105 A1* | 8/2006 | Teeny | A61F 2/4609 |
| | | | 606/76 |
| 2006/0200165 A1* | 9/2006 | Tulkis | A61B 17/1666 |
| | | | 606/99 |
| 2007/0010825 A1* | 1/2007 | Leisinger | A61F 2/4637 |
| | | | 606/99 |
| 2008/0195111 A1* | 8/2008 | Anderson | A61F 2/4609 |
| | | | 606/90 |
| 2010/0262155 A1* | 10/2010 | Teeny | A61F 2/4609 |
| | | | 606/99 |
| 2012/0184964 A1* | 7/2012 | Hudak, Jr. | A61F 2/4609 |
| | | | 606/91 |
| 2015/0196402 A1* | 7/2015 | Kim | A61F 2/4609 |
| | | | 606/81 |
| 2015/0313722 A1* | 11/2015 | Hudak, Jr. | A61F 2/4609 |
| | | | 606/99 |
| 2015/0359641 A1* | 12/2015 | Nic | A61B 17/1637 |
| | | | 606/81 |
| 2016/0100957 A1* | 4/2016 | Lewis | A61F 2/4609 |
| | | | 606/84 |
| 2018/0200073 A1* | 7/2018 | Joo | A61F 2/34 |
| 2019/0105176 A1* | 4/2019 | Slater | A61F 2/4609 |
| 2021/0154025 A1* | 5/2021 | Slater | A61F 2/4609 |

FOREIGN PATENT DOCUMENTS

| | | |
|---|---|---|
| WO | 2017019332 A1 | 2/2017 |
| WO | 2017180602 A1 | 10/2017 |

OTHER PUBLICATIONS

International Search Report regarding PCT/US2017/026975, dated Jul. 28, 2017.
EPO Examination Report dated Dec. 19, 2019 in European Patent Application No. 18184404.4.
EPO European Search Report in European Application No. 18184404, dated Oct. 16, 2018.

\* cited by examiner

ACETABULAR CUP EXTRACTOR

CROSS-REFERENCE TO RELATED APPLICATIONS

This application is a continuation of U.S. patent application Ser. No. 16/087,144 filed Sep. 21, 2018, which is a U.S. national phase application under 35 U.S.C. § 371 of International Patent Application No. PCT/US2017/026975 filed Apr. 11, 2017, which claims the benefit of U.S. Provisional Application No. 62/321,425, filed Apr. 12, 2016, the entire disclosures of each of which are incorporated by reference herein in their entirety.

BACKGROUND OF THE INVENTION

The present invention relates generally to the field of medical device implant extraction tools. In particular, the present invention relates to an acetabular cup extractor.

The acetabular cup is a medical device implant which forms a socket component of a total hip replacement. It is typically composed of two main parts, namely, a metal shell and a non-metal liner. The metal shell can be porous coated for bone ingrowth, or smooth with the intent of being cemented into place. When the hip implant is damaged due to wear, or there is an infection at the site of the implant, or for various other reasons, it needs to be replaced with a new implant. When removing the acetabular cup, bone conservation is of the utmost importance because the bone in the acetabulum is of low density and there are major arteries behind the acetabulum that need to be protected from the extraction tools.

During implant extraction, medical device implant extraction tools are utilized to remove or extract an implant from bone. An acetabular cup extractor is used to cut an area surrounding an acetabular cup implant for extracting the implant from the bone. Current medical device implant extraction tools for removal and extraction are difficult to use and may cause excess stress or unintended damage to the bone surrounding the implant.

Thus, there is still a need in the art for an extraction tool that can attach to an acetabular cup implant so that the implant may be readily removed from the implant site with improved efficiency and minimal stress upon the bone and surrounding area.

BRIEF SUMMARY

In accordance with an exemplary embodiment, the present invention provides an acetabular cup extractor comprising a fastener for securing to an implant and a cutting assembly. The cutting assembly includes a blade spaced from and movably connected to the fastener and a handle operatively connected to the blade.

The fastener further includes a clamping assembly having an elongated shaft and a first clamping portion and a second clamping portion. The first and second clamping portion are each operatively engaged with the elongated shaft for moving between a retracted position and an extended position for attaching to the implant. The exemplary embodiment further includes a biasing member operatively connected to the elongated shaft and at least one of the first and second clamping portions to move the clamping assembly to the extended position. The elongated shaft includes a threaded proximal end and the biasing member threadedly engages the threaded proximal end.

In accordance with the exemplary embodiment, the biasing member is a wedge that slidingly engages a proximal end of the elongated shaft and at least one of the first and second clamping portions. The wedge further includes a recess for receiving the elongated shaft and is threadedly engaged with the elongated shaft. The wedge is trapezoidal prism shaped. When moving to the extended position, the clamping assembly applies a clamping force for securing the fastener to the implant. The clamping force is a radially directed force. Lateral ends of the first and second clamping portions are configured to abut an inner surface of the implant. A trajectory defined by lateral surfaces of the first and second clamping portions defines a circle.

In accordance with the exemplary embodiment, the first clamping portion slidingly engages with the second clamping portion. One of the first and second clamping portions includes a male member and the other of the first and second clamping portions includes a female member engaged with the male member. The elongated shaft further includes a flange abutting the first and second clamping portions and the cutting assembly further includes a bearing connected to the blade. The bearing is an annular bearing and is rotationally coupled to the elongated shaft of the fastener. The cutting assembly further includes a pivot arm pivotably connected to the bearing and the handle. The cutting assembly is releasably attachable to the fastener. The bearing is mounted on the fastener. The blade is configured as a curved blade and is directly attached to the pivot arm. The first and second clamping portions are positioned between the flange and the wedge. Each of the first and second clamping portions include a bottom wall and a substantially vertical wall extending from the bottom wall. The substantially vertical walls of the first and second clamping portions define a recess for receiving a bearing.

BRIEF DESCRIPTION OF THE SEVERAL VIEWS OF THE DRAWINGS

The foregoing summary, as well as the following detailed description of the preferred embodiments of the invention, will be better understood when read in conjunction with the appended drawings. For the purpose of illustrating the invention, there are shown in the drawings exemplary embodiments which are presently preferred. It should be understood, however, that the invention is not limited to the precise arrangements and instrumentalities shown.

In the drawings.

DETAILED DESCRIPTION OF THE INVENTION

Figure 1:
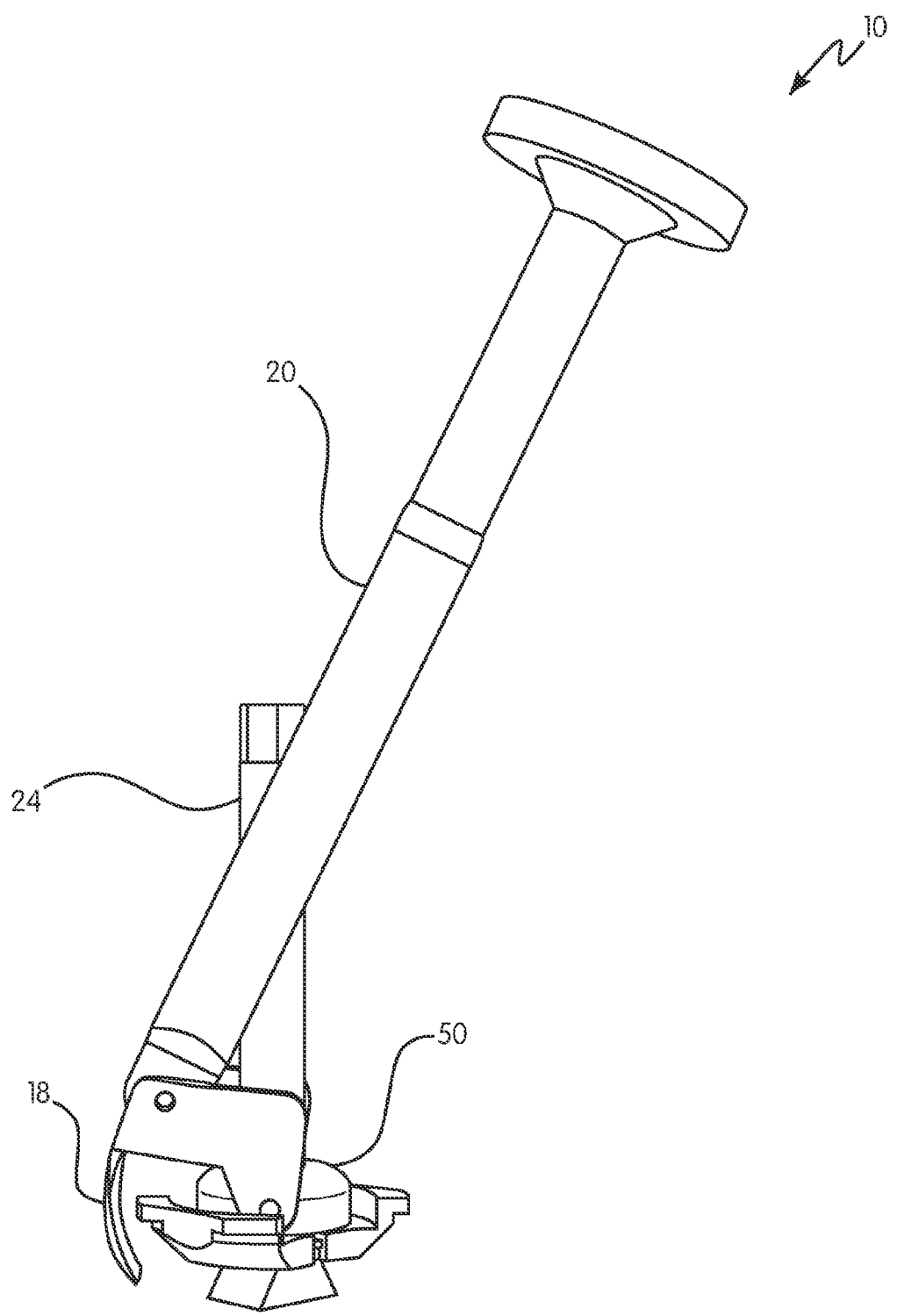
FIG. 1 is a side perspective view of an acetabular cup extractor in accordance with an exemplary embodiment of the present invention.

Reference will now be made in detail to the exemplary embodiments of the invention illustrated in the accompanying drawings. Wherever possible, the same or like reference numbers will be used throughout the drawings to refer to the same or like features. It should be noted that the drawings are in simplified form and are not drawn to precise scale. In reference to the disclosure herein, for purposes of convenience and clarity only, directional terms such as top, bottom, above, below and diagonal, are used with respect to the accompanying drawings. Such directional terms used in conjunction with the following description of the drawings should not be construed to limit the scope of the invention in any manner not explicitly set forth.

Certain terminology is used in the following description for convenience only and is not limiting. The words "right," "left," "lower" and "upper" designate directions in the drawings to which reference is made. The words "inwardly" and "outwardly" refer to directions toward and away from, respectively, the geometric center of the identified element and designated parts thereof. Additionally, the term "a," as used in the specification, means "at least one." The terminology includes the words above specifically mentioned, derivatives thereof, and words of similar import.

"About" as used herein when referring to a measurable value such as an amount, a temporal duration, and the like, is meant to encompass variations of ±20%, ±10%, ±5%, ±1%, or ±0.1% from the specified value, as such variations are appropriate.

Throughout this disclosure, various aspects of the present invention can be presented in a range format. It should be understood that the description in range format is merely for convenience and brevity and should not be construed as an inflexible limitation on the scope of the present invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Furthermore, the described features, advantages and characteristics of the embodiments of the present invention may be combined in any suitable manner in one or more embodiments. One skilled in the relevant art will recognize, in light of the description herein, that the present invention can be practiced without one or more of the specific features or advantages of a particular embodiment. In other instances, additional features and advantages may be recognized in certain embodiments that may not be present in all embodiments of the present invention.

References to proximal elements described herein refer to being closer to the acetabular cup implant or center of the patient, while references to distal elements refer to being further from the acetabular cup implant or the patient. References to the geometric orientation of the elements of the embodiments of the present invention with respect to the patient or acetabular cup implant are approximate, with appropriate adjustment of the acetabular cup extractor understood to be available depending on the needs of the patient.

Figure 2:
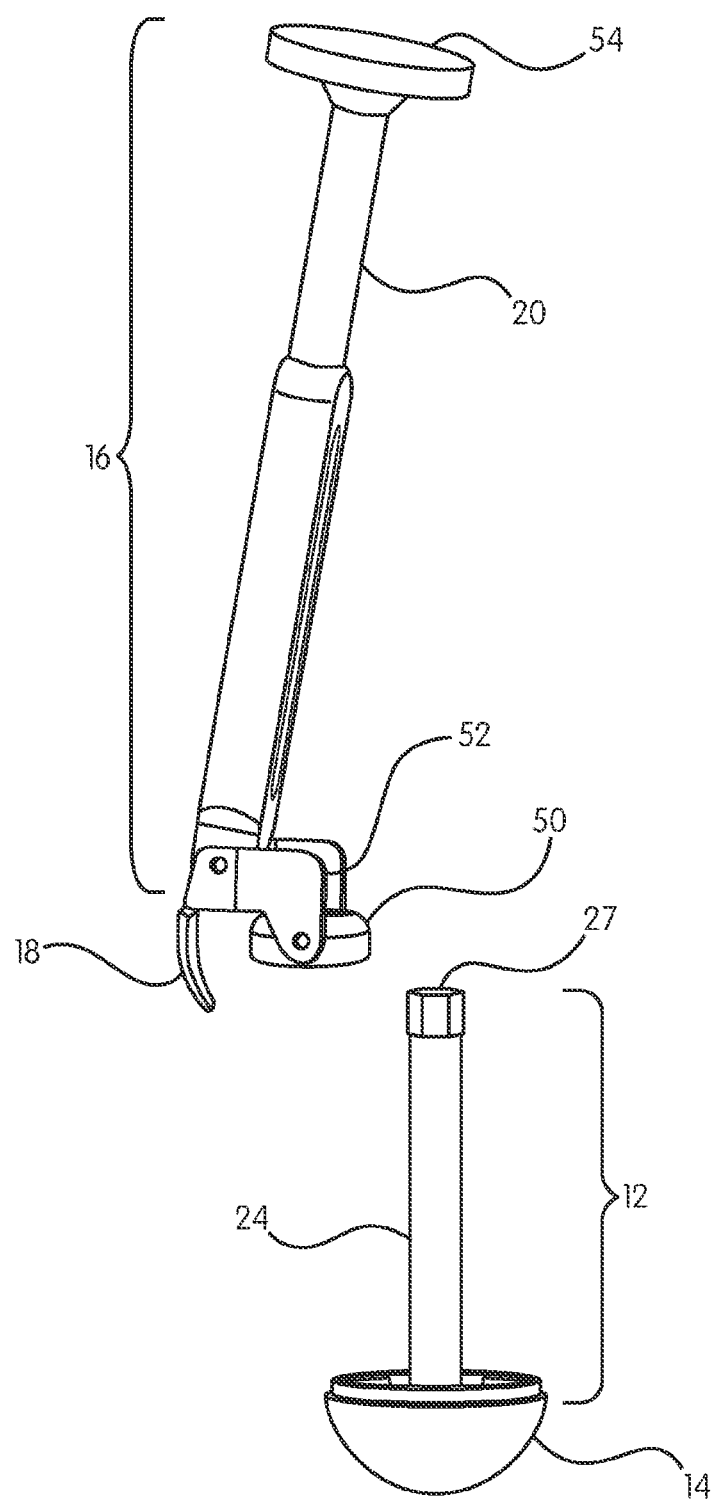
FIG. 2 is a side perspective view of a fastener and a cutting assembly of the acetabular cup extractor of FIG. 1.

FIGS. 1 and 2 illustrate an exemplary embodiment of an implant extraction device 10 in accordance with the present invention. Specifically, the implant extraction device 10 is configured as an acetabular cup extractor. In accordance with an aspect of the present embodiment, the acetabular cup extractor 10 includes a fastener 12 for securing to an implant 14 and a cutting assembly 16. The cutting assembly 16 further includes a blade 18 spaced from and movably connected to the fastener 12 and a handle 20 operatively connected to the blade.

Figure 1A:
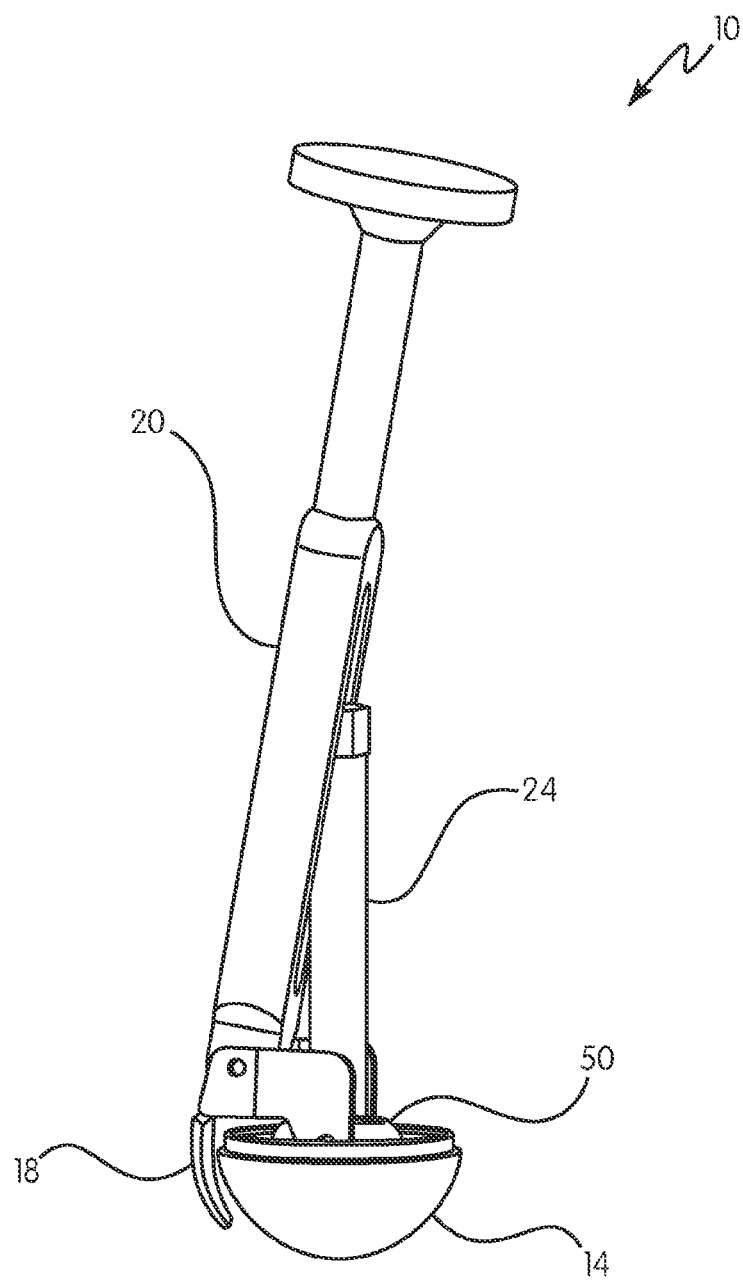
FIG. 1A is a side perspective view of an acetabular cup extractor in accordance with an exemplary embodiment of the present invention attached to an acetabular cup.

As shown in FIGS. 1-5, the fastener 12 includes a clamping assembly 22 for securing to the implant 14 (FIG. 1A). The clamping assembly 22 includes an elongated shaft 24, a first clamping portion 26, a second clamping portion 28 and a biasing member 30. First and second clamping portions 26, 28 are each operatively engaged with the elongated shaft 24 for moving between a retracted position (FIG. 4) and an extended position (FIG. 4A) for attaching to the implant 14.

The elongated shaft includes a distal end 25 about a first end of the elongated shaft 24 for securing to a handle (not shown), and a threaded proximal end 32 about a second end of the elongated shaft 24 opposite the first end. The elongated shaft further includes a flange 48 positioned along a length of the elongated shaft 24 and adjacent the threaded proximal end 32 for engaging the first and second clamping portions 26, 28.

Figure 5:
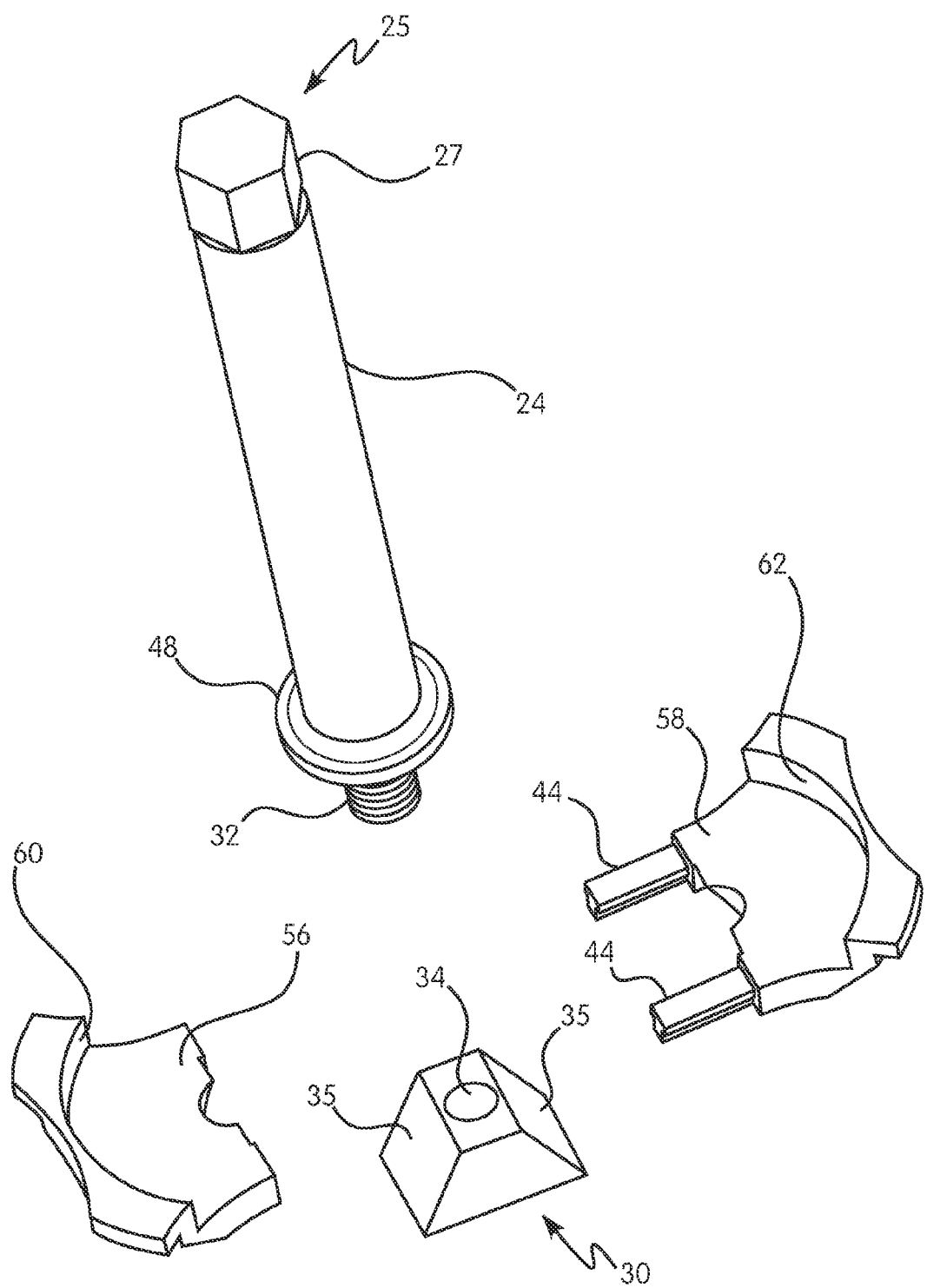
FIG. 5 is an exploded perspective view of the fastener of the acetabular cup extractor of FIG. 1.

As best shown in FIG. 5, the elongated shaft 24 is generally a cylindrical member having a longitudinal central axis and a circular cross-section. However, the elongated shaft 24 can have any shape cross-section such as hexagonal, polygonal or any other shape suitable for its intended purpose. The elongated shaft 24 can also be formed with a plurality of shaft segments having different cross-sectional diameters. However, the elongated shaft 24 preferably has a uniform cross-sectional diameter.

The distal end 25 is configured to receive a tool or handle configured to impart rotating torque, including but not limited to a chuck, or collet (or some other means for imparting torque). As such, a cross-sectional shape of the distal end 25 can be circular, hexagonal, polygonal or any other shape suitable for facilitating application of rotational torque to the threaded proximal end 32.

The distal end 25 preferably includes a hexagonal portion 27 proportioned to fit into a standard chuck or handle rotationally and axially. Optionally, the distal end 25 can include a necked portion in order to help locate the acetabular cup extractor in certain types of standard chucks or handles. The hexagonal portion 27 is configured so that it may be turned by hand or by tool e.g., to fasten the acetabular cup extractor 10 to the implant 14.

As further discussed below, the threaded proximal end 32 is sized and configured to pass through an aperture 65 defined by the first and second clamping portions 26, 28 and configured to engage a threaded recess 34 on the biasing member 30.

The flange 48 is a radially extending flange that circumscribes the elongated shaft 24 along its length and extends transverse to a longitudinal direction of the elongated shaft 24. The flange 48 has a diameter larger than the diameter of the portion of the elongated shaft 24 located above the flange and below the flange. Additionally, the diameter of the flange 48 is greater than the diameter of the aperture 65 defined by the first and second clamping portions 26, 28. With these relative dimensions, the flange 48 allows the threaded proximal end of the elongated shaft 24 to pass through the aperture 65 while limiting further axial movement of the elongated shaft 24 beyond the flange 48. Preferably, the flange 48 is a radially outwardly extending circular flange, but may be any shaped flange suitable for its intended purpose.

Generally, the elongated shaft 24 is illustrated as straight, although it may have a lordotic curve or be otherwise bent or curved. The elongated shaft 24 may have any desired length sufficient for its intended purpose.

Figure 3:
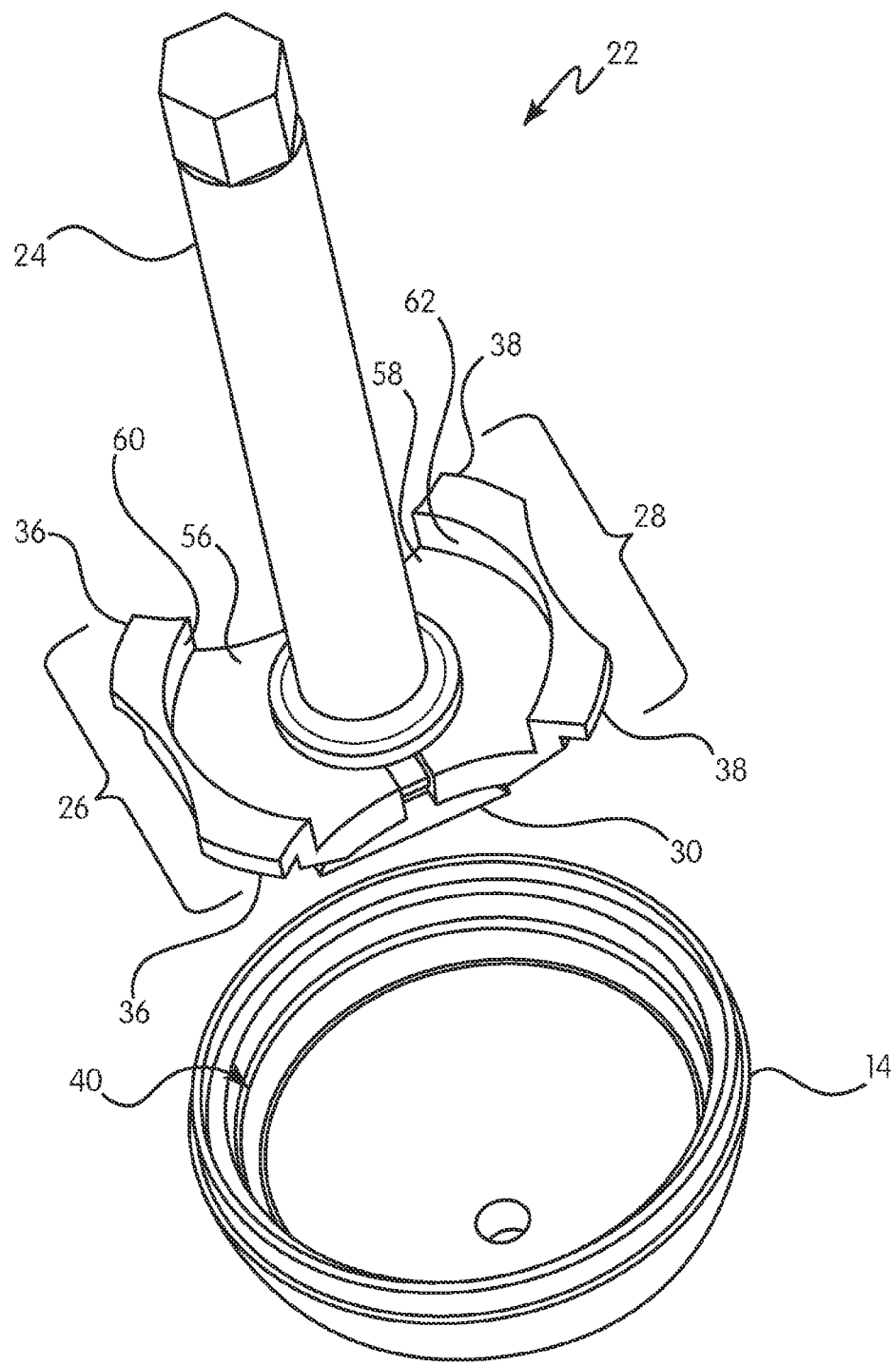
FIG. 3 is a perspective view of the fastener of the acetabular cup extractor of FIG. 1.
Figure 4:
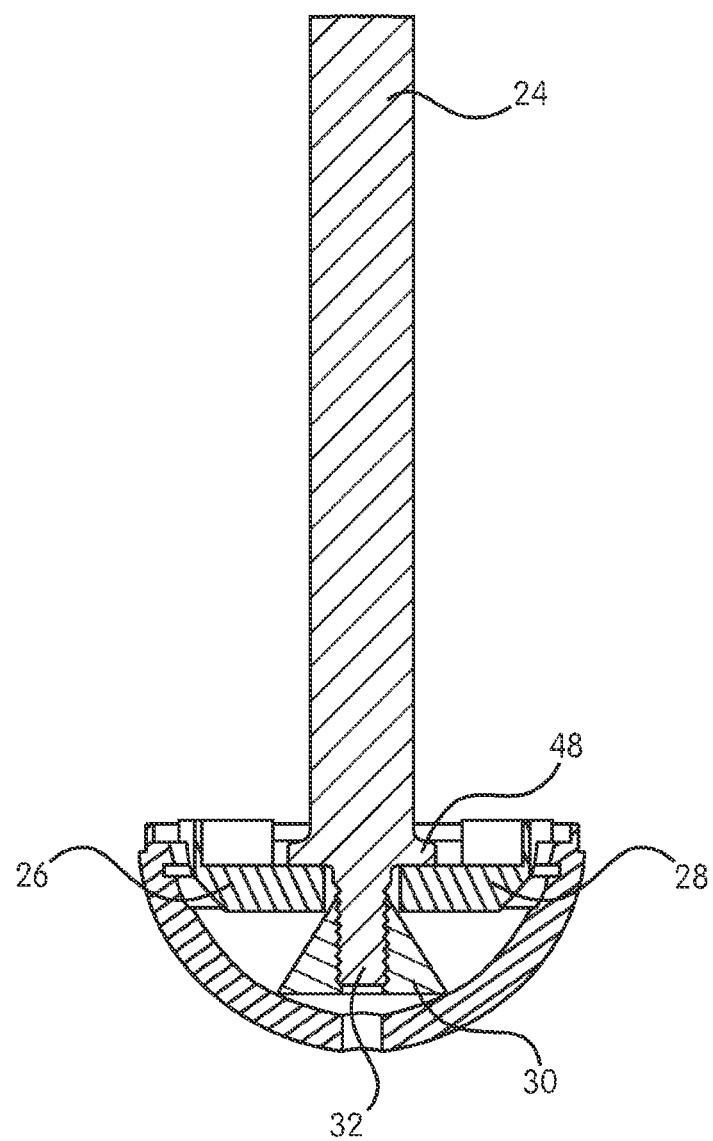
FIG. 4 is a cross-sectional side view of the fastener of FIG. 3 in a retracted position.
Figure 4A:
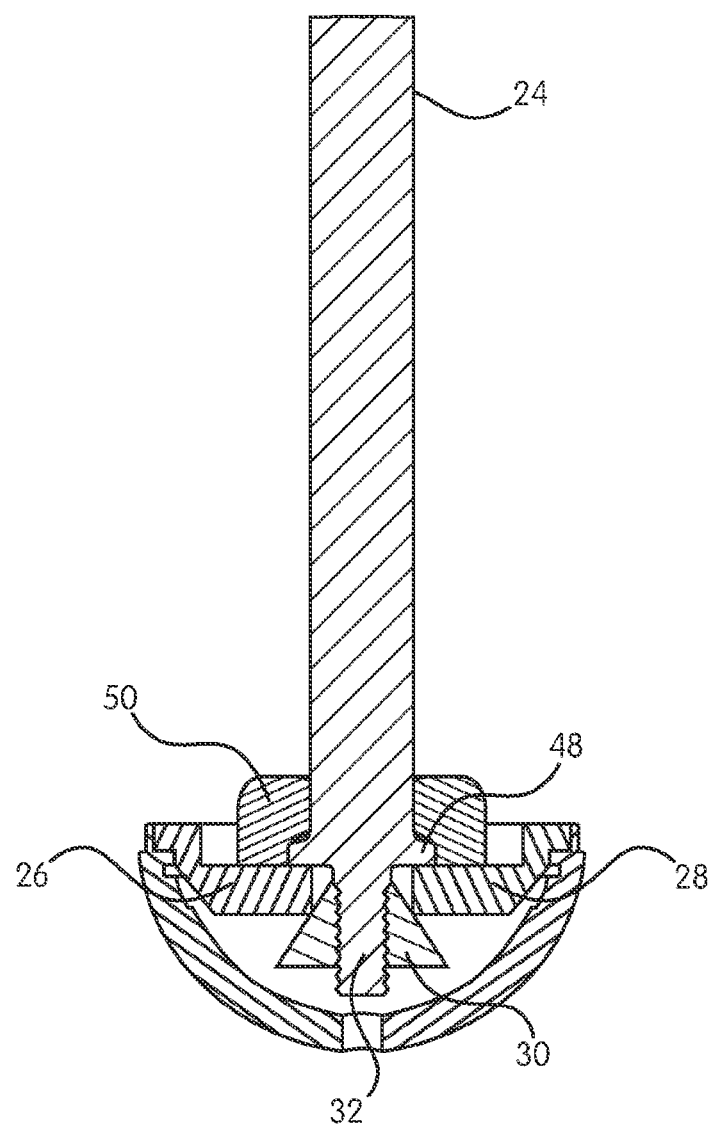
FIG. 4A is a cross-sectional side view of the fastener of FIG. 3 in an extended position.

Referring now to FIGS. 3-6, the first clamping portion 26 and second clamping portion 28 are each operatively engaged with the elongated shaft 24 for moving between a retracted position and an extended position for securing the fastener to the implant 14. As the first and second clamping portions 26, 28 move from the retracted position to the extended position, the first and second clamp portions 26, 28 move farther apart from one another. Conversely, as the first and second clamping portions 26, 28 move from the extended position to the retracted position, the first and second clamping portions 26, 28 move closer to each other. FIGS. 4 and 4A show cross-sections of the fastener 12 of the acetabular cup extractor 10. In the extended position (FIG. 4A), the first clamping portion 26 and second clamping portion 28 are configured to abut an inner surface of the implant 14 for securing the fastener 12 to the implant 14.

Figure 5A:
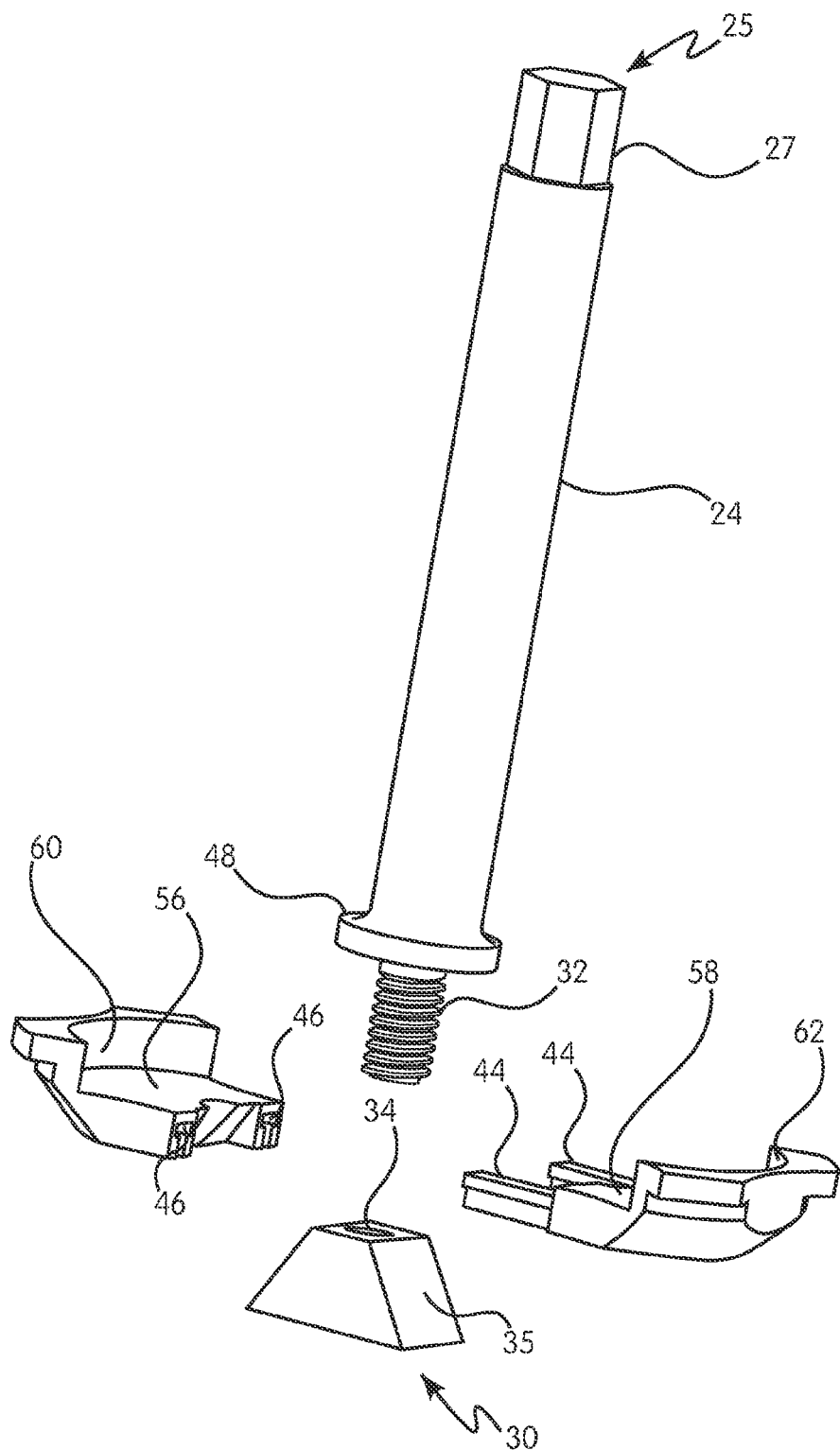
FIG. 5A is another exploded perspective view of the fastener of the acetabular cup extractor of FIG. 1.
Figure 6:
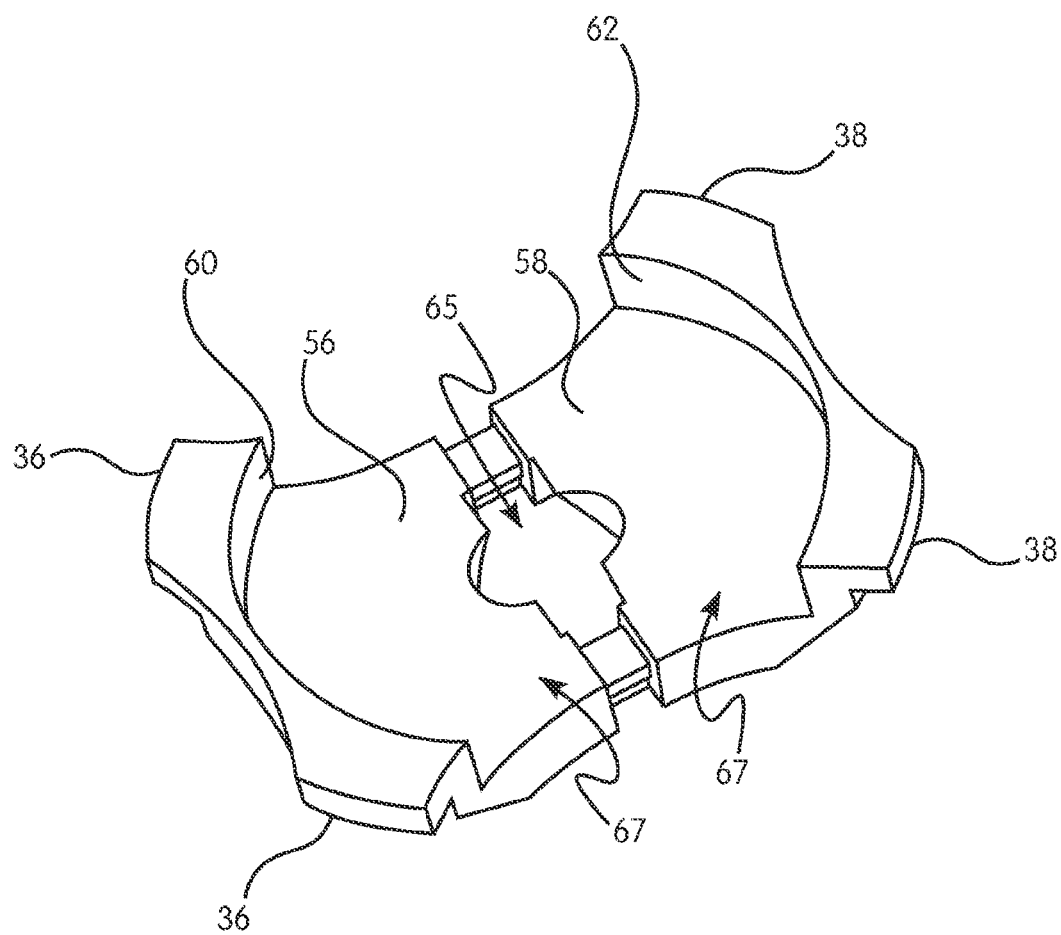
FIG. 6 is a perspective view of a clamping assembly of the acetabular cup extractor of FIG. 1.

In accordance with an exemplary embodiment of the present invention, the first and second clamping portions 26, 28 are configured as shown in FIGS. 5, 5A and 6. The first clamping portion 26 slidingly engages with the second clamping portion 28. As shown in exploded views of the clamping assembly in FIGS. 5 and 5A, one of the first and second clamping portions includes a male member 44 and the other of the first and second clamping portions includes a female member 46 configured to engage with the male member 44. FIG. 6 illustrates the first and second clamping portions 26, 28 in the retracted position. In an aspect, a trajectory defined by lateral ends 36, 38 of the first and second clamping portions 26, 28 define a circle.

Each of the first and second clamping portions 26, 28 include a bottom wall 56, 58 and a substantially vertical wall 60, 62 extending from the bottom wall 56, 58. As shown in FIG. 6, the first clamping portion 26 is connectable to the second clamping portion 28 such that they collectively form the aperture 65 for receiving the elongated shaft 24 therethrough. As shown in FIGS. 4 and 4A, the flange 48 rests upon the bottom walls 56, 58 of the respective first and second clamping portions 26, 28. The aperture 65 has a cross-sectional shape which is sized and configured for receiving the elongated shaft 24 therein. As best shown in FIG. 3, when the clamping assembly is in a retracted position, first and second clamping portions 26, 28 are collectively disposed around the elongated shaft 24.

In accordance with an exemplary embodiment of the present invention, the biasing member 30 is configured as best shown in FIGS. 4, 5 and 5A. The biasing member 30 is operatively connected to the elongated shaft 24 and abuts at least one of the first and second clamping portions 26, 28 to move the clamping assembly 22 to the extended position. As best shown in FIGS. 4 and 4A, the biasing member 30 is disposed below and adjacent each of the first and second clamping portions 26, 28. Specifically, the biasing member is loosely secured in position against the underside of the first and second clamping portions 26, 28. The threaded proximal end 32 is configured to engage the biasing member 30 such that the elongated shaft 24 firmly grips the biasing member 30.

In an exemplary embodiment illustrated in FIGS. 5 and 5A, the biasing member 30 is configured as a wedge. Preferably, the wedge 30 includes a pair of inclined wedge surfaces 35 for biasing the first and second clamping portions 26, 28 toward the extended position. As previously discussed, the wedge 30 includes recess 34 for receiving the elongated shaft 24. The recess 34 is positioned between the pair of inclined wedge surfaces 35. The recess 34 preferably has a cylindrical internal wall with female threads for threadedly engaging the threaded proximal end 32 of the elongated shaft 24. Generally, the wedge 30 slidingly engages the threaded proximal end 32 of the elongated shaft 24 and slidingly engages at least one of the first and second clamping portions 26, 28.

Referring now to FIGS. 4 and 4A, the wedge 30 is threadedly engaged with the threaded proximal end 32 of the elongated shaft 24. In the extended position, the wedge 30 biases diametrically opposed inner surfaces of the first and second clamping portions 26, 28 away from each other toward an inner surface of the implant 14 when positioned within the acetabular cup. When the wedge 30 is pressed towards the aperture 65 between the first clamping portion 26 and second clamping portion 28, the first and second clamping portions 26, 28 move away from each other. As the first and second clamping portions 26, 28 move away from one another, the lateral ends 36, 38 of the first and second clamping portions 26, 28 abut an inner surface 40 of the implant 14, thereby securing the fastener 12 to the implant 14.

When moving to the extended position, the clamping assembly 22 applies a clamping force through the first and second clamping portions 26, 28. The clamping force is a radially directed force that secures the fastener 12 onto the inner surface 40 of the implant 14. As the elongated shaft 24 is rotated, the threaded proximal end 32 threadedly engages the recess 34 of the wedge 30 such that the wedge 30 moves upward toward an under surface of the first and second clamping portions 26, 28. As such, the inclined wedge surfaces 35 bias the diametrically opposed inner surfaces of the first and second clamping portions 26, 28 away from each other. The pair of inclined wedge surfaces 35 are sloped in the proximal direction so as to assist in biasing the inner surfaces of the first and second clamping portions 26, 28. The elongated shaft 24 is rotated until the lateral ends 36, 38 of the first and second clamping portions 26, 28 fixedly attach to the inner surface 40 of the implant 14. The inner surface of the implant 14 may include a plurality of finger slots, depressions or grooves complementary to the lateral ends 36, 38 of the first and second clamping portions 26, 28 to facilitate in securing the clamping assembly to the implant 14. FIG. 4A illustrates a cross-sectional view of the fastener secured to the implant in the extended position. In the extended position, the fastener is rigidly fixed in place relative to the implant.

As configured and shown in FIGS. 3-5, the biasing member 30 is preferably configured as a trapezoidal prism shaped wedge. However, the biasing member 30 can alternatively be an elastomeric member, a clock spring or any other biasing member suitable for its intended purpose.

In operation, when the elongated shaft 24 is inserted into the aperture 65 formed by the first and second clamping portions 26, 28 and threadedly engages the recess 34 of the biasing member 30, the elongated shaft 24 is turned using a surgical tool adapted to fit the hexagonal portion 27 of the distal end 25. As the elongated shaft 24 is rotated, the threaded proximal end 32 engages screw threads in the biasing member. As a result, the biasing member 30 is moved upwardly and causes outwardly movement of the first and second clamping portions 26, 28. The outwardly movement of the first and second clamping portions allow a clamping force to be delivered such that lateral ends 36, 38 of the first and second clamping portions 26, 28 abut respective inner surfaces 40 of the implant 14. Specifically, the first and second clamping portions 26, 28 apply a force to the inner surface 40 of the implant 14 along an axis substantially transverse to a longitudinal axis of the elongated shaft. As a result, the fastener of the acetabular cup extractor is secured to the implant.

In sum, when the elongated shaft 24 is inserted into the recess between the first and second clamping portions 26, 28 and the recess of the wedge 30, the elongated shaft 24 is turned using a surgical tool adapted to fit the hexagonal end 27 of the elongated shaft 24, engaging the threaded proximal end 32 with the threaded recess of the wedge so that the inclined wedge surfaces 35 bias the first and second clamping portions 26, 28 toward the extended position where the lateral edges of the clamping portions 26, 28 latch onto the inner surface of the implant for securing the fastener to the implant 14.

Figure 7:
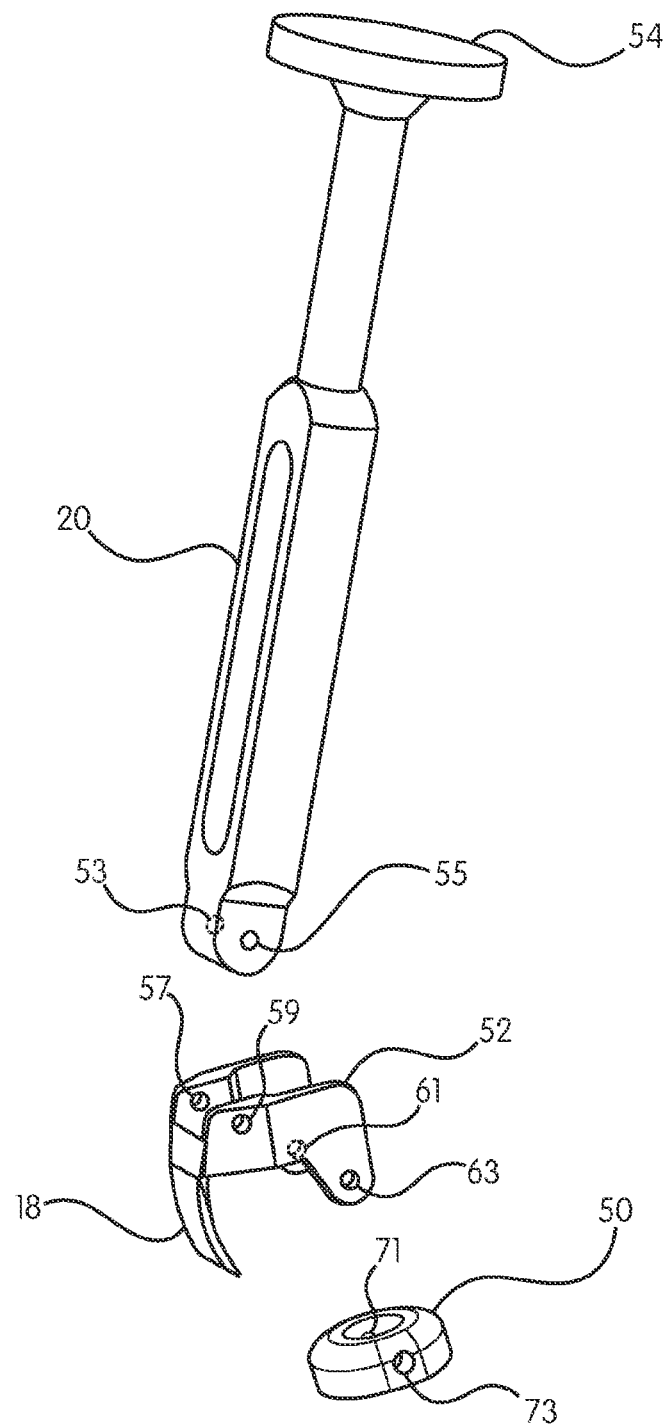
FIG. 7 is an exploded perspective view of the cutting assembly of the acetabular cup extractor of FIG. 1.

In accordance with an exemplary embodiment of the present invention, the cutting assembly 16 is configured as shown in FIGS. 1, 2 and 7. The cutting assembly 16 includes a blade 18 spaced from and movably connected to the fastener 12 and a handle 20 operatively connected to the blade 18. The cutting assembly 16 further includes a pivot arm 52 directly connected to the blade 18. As further discussed below, the pivot arm 52 is pivotably connected to the handle 20 and a bearing 50 for rotatably mounting the cutting assembly 16 to the elongated shaft 24 of the fastener 12.

The handle 20 includes an impact surface 54 about a distal end of the handle 20 for receiving a driving force from a surgical tool such as a hammer. The impact surface 54 is generally shaped as a planar member configured to receive an impact force from a surgical tool. In an aspect, an impact force on the impact surface 54 is transferred to the blade 18. Specifically, an impact force upon the impact surface 54 results in a downward directed force on the blade, for example, for procedures involving cutting away portions of bone from an implanted acetabular cup.

The impact surface 54 is configured as best shown in FIGS. 1-3, but can alternatively be configured as any other structure suitable to allow the transfer of forces acting on the impact surface 54 to the blade 18. In operation, the impact surface is configured to receive a downward force substantially parallel to a longitudinal axis of the handle 20.

The handle 20 is generally an elongated member that is preferably rigid and sized sufficiently to receive a hand of a user. Additionally, the handle 20 is sized sufficiently to allow clearance between a surgical tool, e.g., a hammer, providing a downward force on the impact surface 54 and a hand of a user on the handle 20 while avoiding interference with the elongated shaft 24 of the fastener. Preferably, the handle 20 is substantially tubular but may be any shape suitable for its intended purpose e.g., cubical, cylindrical, conical and the like.

The handle 20 may include gripping portions that aid a user's ability to grip and move the handle. The gripping portion is preferably disposed throughout the length of the handle 20 to aid in gripping the handle. The gripping portion may be shaped as any suitable shape that may aid a user's ability to grip and move the handle such as finger slots, depressions, grooves or a textured surface.

FIG. 7 shows an exploded perspective view of the blade 18 applicable to the acetabular cup extractor 10 of the present invention. Although the blade 18 is configured and shown as directly attached to or integrally formed with the pivot arm 52, the blade can be removably attached from the pivot arm 52. For example, it is to be understood that the blade 18 could be attached to the pivot arm 52 via apertures and dowels for connecting two or more elements. However, instead of apertures and dowels, alternative mechanisms for connecting two or more elements such as, for example, screws, bolts, rivets and the like may be used.

Preferably, the blade 18 is a curved blade. As shown in FIG. 1, the curved blade 18 corresponds to a hemispherical shape of an acetabular cup. However, the acetabular cup extractor 10 is configured to receive a variety of blades having variable lengths corresponding to difference sized acetabular cup implants. For example, the blade 18 can have a predetermined length corresponding to a patient-specific sized acetabular cup implant. The blade 18 can be sized and shaped with any thickness or width suitable for being pivotably connected to the fastener. Preferably, the blade 18 includes a beveled edge for driving the blade 18 into a hemispherical area surrounding an acetabular cup implant while minimizing bone damage to surrounding areas. In general, the blade 18 will have smaller and larger variations as well as different degrees of curvature to accommodate various implants.

Referring now to FIG. 2, the pivot arm 52 includes a first end pivotably connected to the handle 20 and a second end spaced from the first end. The second end of the pivot arm 52 is pivotably connected to the bearing 50. Specifically, the first end of the pivot arm 52 is pivotably connected to the proximal end of the handle 20 opposite the impact surface 54. As further discussed below, the pivot arm 52 allows movement of the handle 20 relative to the clamping assembly 22. When the acetabular cup extractor is fully assembled (FIG. 1), the pivot arm 52 is pivotably connected to the bearing 50 such that the cutting assembly 16 is rotationally coupled to the fastener 12.

Figure 8:
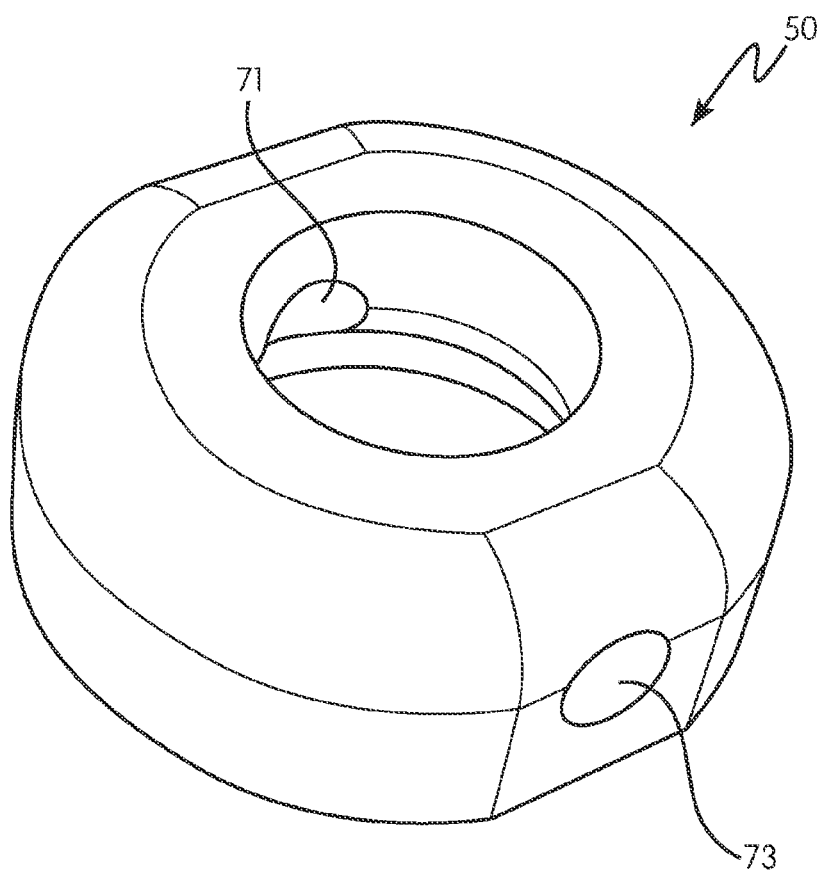
FIG. 8 is a top perspective view of a bearing of the acetabular cup extractor of FIG. 1.
Figure 9:
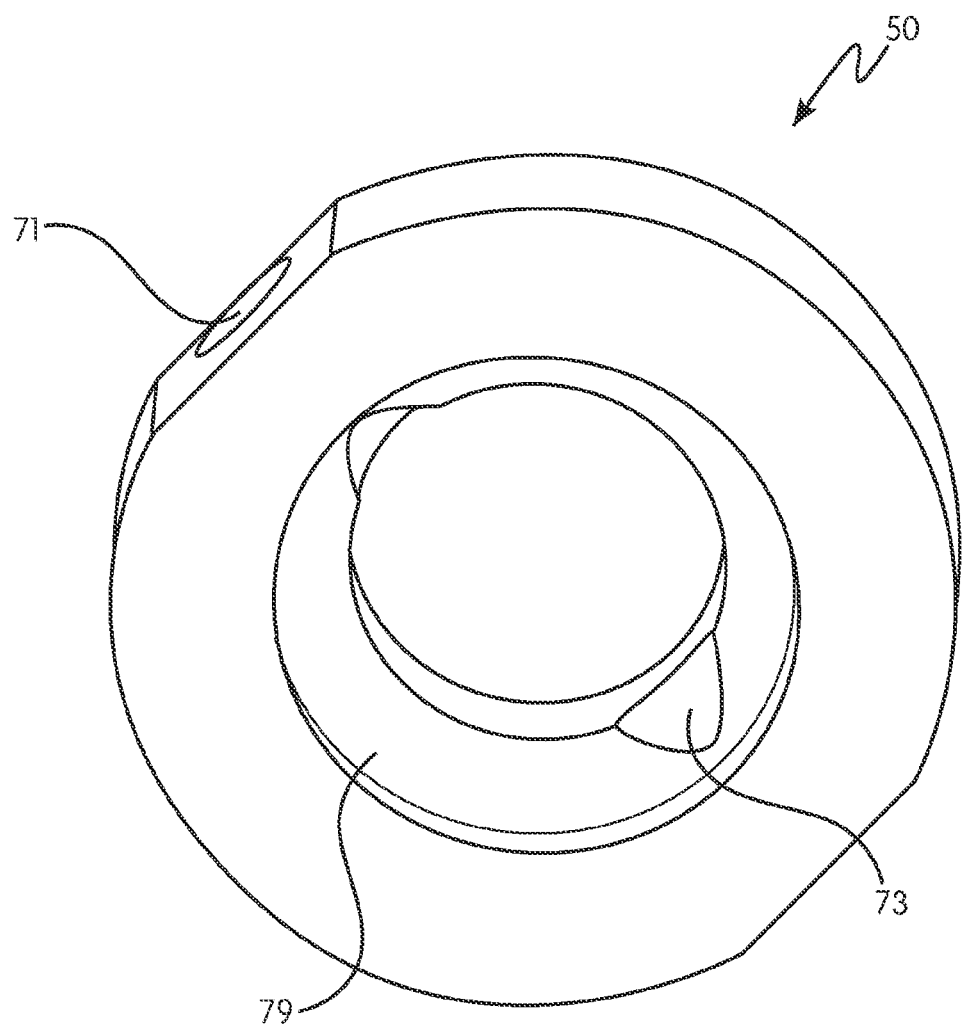
FIG. 9 is a bottom perspective view of the bearing of FIG. 8.

As shown in FIGS. 7-9, the pivot arm 52 includes a pair of apertures 57, 59 corresponding with a pair of apertures 53, 55 on the handle 20, both for receiving fasteners for pivotably connecting the handle 20 and the pivot arm 52. Similarly, the pivot arm 52 includes a pair of apertures 61, 63 corresponding with a pair of apertures 71, 73 on the bearing 50, both for receiving fasteners for pivotably connecting the bearing 50 and the pivot arm 52. However, instead of apertures and fasteners, alternative mechanisms for pivotably connecting two more elements may be used.

Referring now to FIGS. 1, 2, 7, 8 and 9, the bearing 50 is configured as shown. Preferably, the bearing 50 is configured as an annular bearing. As shown in FIG. 1, the bearing is rotationally coupled to the elongated shaft 24 of the fastener 12. Specifically, the bearing 50 is mounted onto the elongated shaft 24 of the fastener 12 such that the bearing 50 is positioned adjacent a superior surface of the flange 48.

As previously discussed, when the first clamping portion 26 and second clamping portion 28 are secured together (FIG. 6), the bottom walls 56, 58 collectively form a cavity 67. The bearing 50 is mounted within the cavity 67 defining a pivot joint. Preferably, a bottom surface of the bearing 50 and flange 48 are arcuate in shape such that the cutting assembly can be efficiently assembled with the fastener so that the bearing 50 is held in place inside the cavity 67. The bottom surface of the bearing 50 (FIG. 9) is further configured to overlap the flange 48 and be in communication with the bottom walls 56, 58 forming the cavity 67. Specifically, the bottom surface of the bearing 50 includes an annular relief 79 for receiving the flange 48. The shape of annular relief 79 corresponds to the shape of the flange 48. It is to be appreciated by those skilled in the art that the bearing 50 can be securely held in place inside the cavity 67 in a number of ways including, but not limited to, screws, welding, hooks, clasps, grooves, rivets and so forth.

Although the bearing 50 is seated in the cavity 67 of the clamping assembly 22, the outer surface of the bearing 50 is spaced from vertical walls 60, 62 of the first and second clamping portions 26, 28 to allow the bearing 50 to freely rotate around the elongated shaft 24. Specifically, the elongated shaft 24 acts as a central rotational axis for the bearing 50 such that the cutting assembly 16 can be freely rotated about the fastener 12 during operation.

As shown in FIGS. 1 and 2, the cutting assembly 16 is releasably attachable to the fastener 12. FIG. 2 illustrates the cutting assembly 16 and fastener 12 before the acetabular cup extractor 10 is fully assembled. As best shown in FIGS. 3 and 4 and previously discussed, the fastener 12 is secured to the implant 14 by the clamping assembly 22. Specifically, the elongated shaft 24 is rotated by a user until the clamping assembly fixedly attaches to the inner surface of the implant 14.

Thereafter, the cutting assembly 16 is mounted onto the fastener 12. Specifically, the bearing 50 is rotationally coupled to the elongated shaft 24. As shown in FIG. 1, the blade 18 is spaced from the implant 14 but disclosed adjacent an outer hemispherical surface of the implant 14. As previously discussed, different sized blades can be used to accommodate different sized acetabular cup implants. The blade 18 is closely spaced to the outer hemispherical surface of the implant 14 to minimize bone loss.

During operation, the handle 20 is used to drive the blade 18 around the outer surface of the implant 14 to break up any bone ingrowth or cement to implant interface. The area around the implant 14 is broken up by rotating the blade 18 via the handle such that the blade travels around the perimeter of the implant 14. The handle 20 pivots about the blade 18 to allow a user to work at an efficient angle when driving the blade into the bone ingrowth. Additionally, an impact force can be applied to the impact surface 54 of the handle 20 to drive the blade through any bone or cement. For example, an impact force 54 can be supplied by a surgical tool such as a hammer to allow a surgeon to drive a blade 18 deeper into a bone or implant area. Once the area surrounding the hemispherical outer surface of the implant is cleaned by driving the blade deeper and around the implant 14, the cutting assembly 16 is removed from the elongated shaft 24 of the fastener.

After bone surrounding the implant is cut away, a user can grasp the elongated shaft 24 to apply torque to the implant for removal purposes. Alternatively, a surgical tool can be used to attach to the elongated shaft to remove the implant 14 from a patient.

While the present invention has been described with reference to preferred embodiments, it will be appreciated by those skilled in the art that various changes may be made and equivalents may be substituted for elements thereof without departing from the scope of the present invention. In addition, modifications may be made to adapt a particular situation or material to the teachings of the present invention without departing from the essential scope thereof. It is to be understood, therefore, that the present invention not be limited to the particular aspects disclosed, but it is intended to cover modifications within the spirit and scope of the present invention as disclosed.

I claim:
1. An acetabular cup extractor comprising:
a fastener for contacting an implant, the fastener having an overall width sized for seating within the implant;
a cutting assembly that includes:
a blade spaced from the fastener a predetermined spacing;
an adjustment member operatively configured to adjust the predetermined spacing; and
a handle operatively connected to the cutting assembly.
2. The acetabular cup extractor of claim 1, wherein the adjustment member includes threads.
3. The acetabular cup extractor of claim 1, wherein the adjustment member moves one of the fastener and cutting assembly relative to the other of the fastener and cutting assembly.
4. The acetabular cup extractor of claim 1, wherein one of the fastener and blade moves laterally relative to the other of the fastener and blade.
5. The acetabular cup extractor of claim 1, wherein the fastener includes a shaft.
6. The acetabular cup extractor of claim 5, wherein the adjustment member is operatively connected to the shaft.

* * * * *